United States Patent [19]

Enomoto et al.

[11] 4,415,570
[45] Nov. 15, 1983

[54] NICOTINIC ACID DERIVATIVES

[75] Inventors: Hiroshi Enomoto, Nagaokakyo; Akira Nomura, Hirakata; Yoshiaki Aoyagi, Otsu; Yoshihisa Shibata, Kameoka, all of Japan

[73] Assignee: Nippon Shinyaku Co. Ltd., Japan

[21] Appl. No.: 383,703

[22] Filed: Jun. 1, 1982

[30] Foreign Application Priority Data

Jun. 5, 1981 [JP] Japan .................................. 56-87124

[51] Int. Cl.³ ...................... A61K 31/53; C07D 401/12
[52] U.S. Cl. ................................ 424/249; 424/248.54; 544/113; 544/207
[58] Field of Search .......................... 424/249, 248.54; 544/113, 207

[56] References Cited

U.S. PATENT DOCUMENTS 3,271,393  9/1966  Ueda et al. .......................... 544/113
4,317,822  3/1982  Woltersdorf et al. .............. 544/207

Primary Examiner—John M. Ford

Attorney, Agent, or Firm—Jacobs & Jacobs

[57] ABSTRACT

Compounds useful in the treatment of rheumatism or allergic nephritis which have the formula

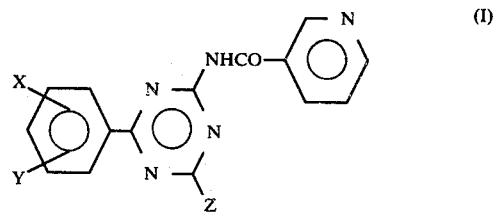

wherein
X is halogen, hydroxy, lower alkyl, lower alkenyl, lower alkoxy, nitro or amino;
Y is hydrogen, halogen, hydroxy, lower alkyl, lower alkenyl, lower alkoxy, nitro or amino; and
Z is mono-(lower alkyl)amino, di-(lower alkyl)amino, piperidino, piperazino, pyrrolidino, or morpholino.

7 Claims, No Drawings

NICOTINIC ACID DERIVATIVES

The present invention relates to nicotinoylbenzoguanamine derivatives of formula (I):

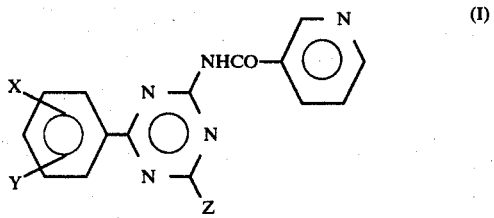

and pharmaceutically acceptable acid addition salts thereof, wherein
- X is halogen, hydroxy, lower alkyl, lower alkenyl, lower alkoxy, nitro or amino;
- Y is hydrogen, halogen, hydroxy, lower alkyl, lower alkenyl, lower alkoxy, nitro or amino; and
- Z is mono-(lower alkyl)amino, di-(lower alkyl)amino, piperidino, piperazino, pyrrolidino, or morpholino.

As used herein, lower alkyl and lower alkoxy each contain 1 to 6, preferably 1 to 4, carbon atoms in a straight or branched chain, and lower alkenyl contains 2 to 6, preferably 2 to 4, carbon atoms in a straight or branched chain. The term halogen preferably denotes fluorine, chlorine, bromine and iodine, most preferably fluorine, chlorine and bromine.

In a preferred embodiment of the invention, X is halogen and Y is hydrogen or halogen. Most preferably X is chlorine and Y is hydrogen or chlorine, or X is fluorine and Y is hydrogen. Preferably, Z is dimethylamino, diethylamino or butylamino.

There have been prior proposals of benzoguanamine derivatives, e.g. British Pat. No. 1,441,904, Swiss Pat. No. 596,193, U.S. Pat. No. 4,103,009, British Pat. No. 1,511,218, German Pat. No. 2,713,933 and Japanese published Patent 57-35587. However, we have now found that the compounds (I) of the present invention strongly inhibit a reversed passive Arthus reaction (hereinafter referred to as "RPAR"). Further, the present invention provides a technically advantageous method of preparing the compounds of the present invention.

Compounds (I) according to the present invention are basic substances and form salts with various acidic substances. Examples of pharmaceutically acceptable salts of compound (I) are salts with hydrochloric acid, hydrobromic acid, sulfuric acid, citric acid, malonic acid, tartaric acid, malic acid, maleic acid, fumaric acid, benzoic acid, salicyclic acid, cinamic acid, methanesulfonic acid, benzenesulfonic acid, tosylic acid, nicotinic acid, and the like.

Substances that inhibit RPAR are useful as remedies for rheumatism and for allergic nephritis in clinical fields. Activity of RPAR inhibition of the compounds of the present invention was measured in the following manner.

Anti-BSA serum was obtained from rabbits that were previously administered bovine serum albumin ("BSA"). The anti-BSA serum was applied to four parts of the skin of the abdomens of rats previously treated with BSA and Evans Blue. The anti-BSA serum and the BSA and Evans Blue were administered to the rats subcutaneously.

The prepared rats were divided into two groups, one group serving as a control and the other group being orally administered the test compounds 1-10 of Table 1 below at a dosage of 200 mg/kg body weight. The local inflammation was determined by examining each of the four inflamed parts and measuring for each part the area from which there was leakage of Evans Blue. The data from the test animals were compared to the control animals, and a reduction in the leakage area of 20% or more was defined as a positive effect. The RPAR inhibition activity is reported as the number of positive effects per animal, divided by 4. Thus, two positive effects would be an RPAR of 2/4. The results are reported in Table 1 below, along with an identification of compounds 1-10.

TABLE I

| Compounds | X,Y-phenyl | Z | Melting Point (in centigrade) | RPAR Inhibition |
|---|---|---|---|---|
| (1) | 4-Cl-C₆H₄ | pyrrolidino | 204–206 | 2/4 |
| (2) | 4-Cl-C₆H₄ | morpholino | 243–245 | 2/4 |
| (3) | 3-Cl-C₆H₄ | piperidino | 163–164 | 2/4 |
| (4) | 3-Cl-C₆H₄ | morpholino | 158–160 | 2/4 |
| (5) | 3-Cl-C₆H₄ | pyrrolidino | Amorphous powder | 2/4 |
| (6) | 3,4-diCl-C₆H₃ | CH₃(CH₂)₃NH— | 149–153 | 2/4 |
| (7) | 3,4-diCl-C₆H₃ | (C₂H₅)₂N— | 140–143 | ¾ |
| (8) | 3,4-diCl-C₆H₃ | piperidino | 162–164 | ¾ |

TABLE I-continued

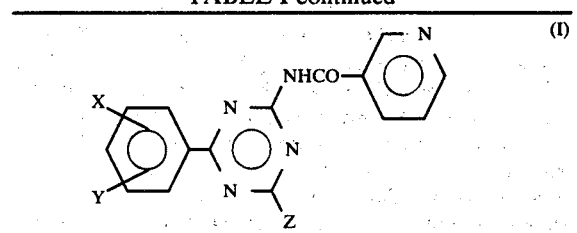

| Compounds | X, Y (phenyl substituents) | Z | Melting Point (in centigrade) | RPAR Inhibition |
|---|---|---|---|---|
| (9) | 2,4-dichlorophenyl | morpholino | 184~187 | 4/4 |
| (10) | 4-fluorophenyl | N(CH₃)₂ | 189~193 | ¾ |

For comparison with the compounds (I) of the invention, compounds 11–17 were subjected to the same tests as described above to determine the RPAR inhibition thereof. The dosages employed and the results obtained are set forth in Table 2 below:

TABLE 2

| Compound | Formula | Dose | RPAR Inhibition |
|---|---|---|---|
| (12) | 2,5-dichlorophenyl-diamino-triazine | 500 mg/kg p.o. | 0/4 |
| (13) | 4-chlorophenyl-diamino-triazine | 500 mg/kg p.o. | 0/4 |
| (14) | phenyl-triazine-NHCO-pyridine, NH₂ | 500 mg/kg p.o. / 200 mg/kg p.o. | 2/4 / 0/4 |
| (15) | 2,6-dichlorophenyl-triazine-NHCO-pyridine, NH₂ | 200 mg/kg p.o. | 0/4 |
| (16) | 4-chlorophenyl-triazine-NHCO-pyridine, NH₂ | 200 mg/kg p.o. | 0/4 |
| (17) | 3-chlorophenyl-triazine-NHCO-pyridine, NH₂ | 200 mg/kg p.o. | 0/4 |

TABLE 2-continued

| Compound | Formula | Dose | RPAR Inhibition |
|---|---|---|---|
| (17) | [structure with I, NHCO, N, NH₂ groups] | 200 mg/kg p.o. | ¼ |

A comparison of Tables 1 and 2 reveals that apparently slight changes in the structure of compound (I) eliminates or sharply reduces RPAR inhibition. Thus, compounds without the nicotinoyl group (compounds 11 and 12 of Table 2) do not exhibit RPAR inhibition activity at all. Compounds in which both X and Y are both hydrogen (compound 13) or those in which Z is unsubstituted amino have little or no RPAR inhibition activity.

The RPAR inhibition activity of the compounds (I) of the present invention is not related to its anti-inflammatory activity. For instance, compound (15) exhibits 56.8 percent carrageenin edema inhibiting activity by intraperitoneal injection (50 mg/kg) but has no RPAR inhibition activity. In contrast, compound (9) strongly inhibits RPAR but its inhibition against carrageenin edema by 50 mg/kg of intraperitoneal injection is only 21 percent. Furthermore, each of phenylbutazone, indomethacin, and aspirin has no RPAR inhibitory action by oral administration thereof at doses of 100, 10 and 200 mg/kg, respectively, and yet each is a well-known anti-inflammatory agent.

Acute toxicity of the compounds according to the present invention is low and, when 2000 mg/kg of any of compounds 1 to 10 is given orally to mice, no animal dies. Thus, the $LD_{50}$ dose is higher than 2000 mg/kg.

The compounds (I) of the present invention may be used for the treatment of humans or other mammals suffering from rheumatism or allergic nephritis, by administering to the sufferer an effective amount of the compound (I) or a pharmaceutically acceptable salt thereof.

The compounds of the invention may be administered as such, but usually they will be administered in the form of a pharmaceutical composition for the treatment of rheumatism or allergic nephritis, comprising an effective amount of the compound (I) of the invention, or a pharmaceutically acceptable salt thereof, in combination with an inert carrier or diluent therefor.

The pharmaceutical compositions of the present invention may contain a major or minor amount, e.g. 0.1% to 99.5%, preferably 0.5% to 90%, of active ingredient as above-defined in combination with a pharmaceutically acceptable, inert diluent or carrier, the carrier comprising one or more solid semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be about 200 to about 2000 mg per day of the compounds (I) or pharmaceutically acceptable salts thereof, preferably from about 300 to about 600 mg. per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carboydrate, as, for example, starch or mannitol. Flavoring, preservative, dispersing and coloring agents can also be present.

Capsules are made by preparing a powder mixture as described above and filling formed gelatin sheaths. Glidants and lubircants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. An an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

While the routes or administration include oral, parenteral (i.e. intramuscular, intraperitoneal and intravenous), and rectal, oral administration is particularly preferred. The preferred pharmaceutical compositions are therefore those in a form suitable for oral administration, such as tablets and liquids.

Compounds I of the present invention may, for example, be synthesized by the following reactions:

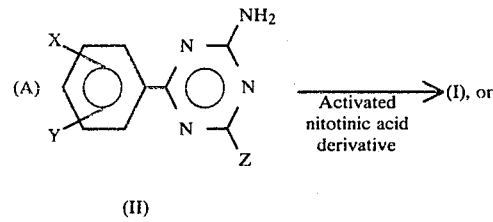

(II)

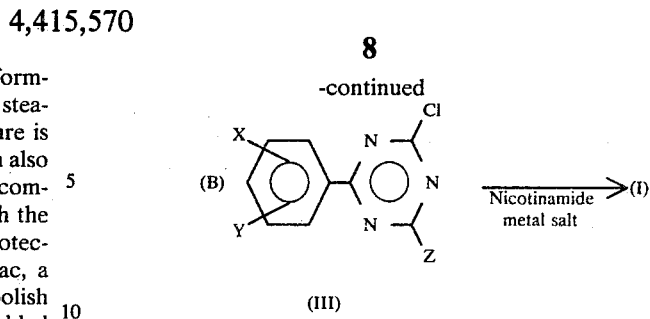

(III)

where X, Y and Z are as defined above.

The starting material II may be obtained by heating dicyandiamide with a substituted amine salt, ZH.HCl (IIa), to give a substituted biguanide (IIb), as shown below. IIb may then be reacted, with heating, with a substituted benzonitrile (IIc) or a (lower alkyl) ester of benoic acid (IIc) to provide compound II. When a substituted benzonitrile is used, a potassium hydroxide catalyst is employed.

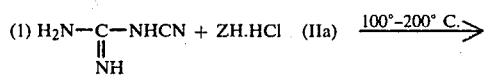

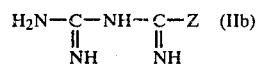

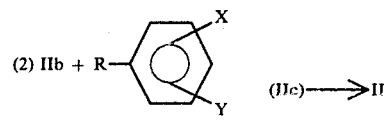

where R is cyanomethyl or loweralkoxycarbonyl.

Compound II may also be prepared by treating a 2,4-dichloro-6-(substituted phenyl)-s-triazine

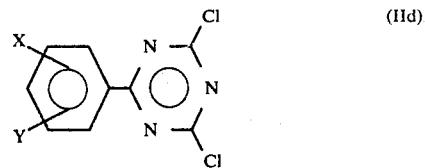

with ammonia to form the 2-amino-3-chloro derivative

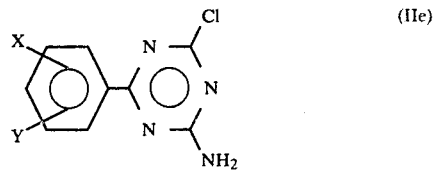

which is then heated with an amine, Z-H (IIf), to provide II.

Examples of activated nicotinic acid derivatives used in the method include nicotinic acid anhydride, nicotinic acid chloride, dichlorophosphoric acid anhydride of nicotinic acid, sulfuric acid anhydride of nicotinic acid, sulfonic acid anhydride of nicotinic acid, and the like and such commonly-used various kinds of activated derivatives can be advantageously used.

When the synthesis is conducted in accordance with route B, the starting material III may be obtained by reacting compound IId with an equimolar amount of the amine IIf in the presence of an acid removing agent to provide compound III, Compound III is, in turn, reacted with nicotinamide sodium salt (prepared from nicotinamide and sodium hydroxide) to provide compound I.

The present invention is illustrated by the following Examples.

EXAMPLE 1

Synthesis of the compounds (1) and (2)

2-Amino-4-chloro-6-(4-chlorophenyl)-s-triazine (melting point 273° to 275° C.) (2.12 grams) and 2.5 grams of pyrrolidine were dissolved in 20 milliliters of dioxane, the mixture was heated to reflux for two hours with stirring, the reaction solution was evaporated to dryness in vacuo, diluted aqueous solution of sodium hydroxide was added to the residue, insoluble matters were collected by filtration, and washed with isopropyl alcohol to give 2.21 grams of 2-amino-4-pyrrolidino-6-(4-chlorophenyl)-s-triazine, melting point 217° to 219° C.

The product obtained here (2.0 grams) was heated to reflux for three hours in 20 milliliters of dioxane together with 1.8 grams of nicotinic acid anhydride. The reaction solution was evaporated to dryness in vacuo and the residue was washed with water and recrystallized from isopropyl alcohol and dioxane mixture to give 1.84 grams of the substance (1). Melting point 204° to 206° C.

When the same reaction was conducted using morpholine instead of pyrrolidine, the compound (2) was obtained.

EXAMPLE 2

Synthesis of the compounds (3), (4), (5) and (10)

Dicyandiamide (8.4 grams) and piperidine hydrochloride (12.1 grams) were heated at 145° to 150° C. for four hours in 20 milliliters of methylcellosolve. After cooled, the reaction solution was mixed with 6.8 grams of sodium ethoxide and 30 milliliters of methylcellosolve, then heated to reflux for four hours with 15 grams of methyl o-chlorobenzoate, cooled, diluted with 200 milliliters of water, the crystals separated out therefrom were collected by filtration, and washed with methanol to give 6.3 grams of 2-amino-4-piperidino-6-(2-chlorophenyl)-s-triazine, melting point 184° to 186° C.

The resulting product (3.6 grams) and 4.6 grams of nicotinic acid anhydride were heated to reflux with stirring for four hours. The reaction solution was evaporated to dryness in vacuo, the residue was dissolved in chloroform, washed with 1 percent aqueous solution of potassium carbonate, the solvent was evaporated therefrom, the residue was dissolved in benzene with warming, and cooled to give crystals which were recrystallized from benzene to give 4.35 grams of the substance (3), melting point 163° to 164° C.

When the same reaction was carried out using morpholine hydrochloride or pyrrolidine hydrochloride instead of piperidine hydrochloride, compounds (4) and (5), respectively, were obtained. When the reaction with dicyandiamide was conducted using dimethylamine hydrochloride and the succeeding reaction was done using p-fluorobenzonitrile, then the compound (10) was obtained.

EXAMPLE 3

Synthesis of the compounds (6) and (7)

2-Amino-4-chloro-6-(3,4-dichlorophenyl)-s-triazine (melting point 249° to 250° C.) (2.75 grams) and 2.0 grams of n-butylamine were heated to reflux with stirring for four hours in 25 milliliters of dioxane. The reaction solution was evaporated to dryness in vacuo, the residue was washed with water and then with methanol, and 2.51 grams of 2-amino-4-butylamino-6-(3,4-dichlorophenyl)-s-triazine was obtained. Melting point 176° to 179° C.

Nicotinic acid (2.5 grams) was added to 10 milliliters of pyridine, 2.7 grams of isobutyl chlorocarbonate was dropped thereinto with ice-cooling and stirring within five minutes, the mixture was stirred for another thirty minutes, then 2.0 grams of the compound as obtained hereinabove was added thereto, and the mixture was stirred under refluxing for three hours. Pyridine was evaporated therefrom under reduced pressure, the residue was dissolved in methanol with warming, and allowed to stand whereupon crystals came out. They were removed by filtration, the mother liquor was concentrated, the resulting syrup was allowed to stand to give crystals. Recrystallization from methanol gave 0.91 gram of the compound (6). Melting point 149° to 153° C.

The same reaction as above was conducted using diethylamine instead of n-butylamine to give 2-amino-4-diethylamino-6-(3,4-dichlorophenyl)-s-triazine, melting point 201° to 204° C. The resulting product (2.0 grams) and 2.5 grams of nicotinic acid were added to 50 milliliters of pyridine, 2.4 grams of methanesulfonyl chloride was dropped thereinto during ten minutes at room temperature with stirring, and the mixture was heated to reflux for three hours. The reaction solution was evaporated to dryness in vacuo, to the residue was added water, insoluble matters were collected by filtration, and they were washed with methanol and recrystallized form isopropyl alcohol to give 1.25 grams of the substance (7), melting point 140° to 143° C.

EXAMPLE 4

Synthesis of the compounds (8) and (9)

2,4-Dichloro-6-(2,5-dichlorophenyl)-s-triazine (3.0 grams) was dissolved in 50 milliliters of ether and, with stirring and ice cooling, 1.70 grams of piperidine was dropped thereinto during five minutes. After the mixture was stirred for one hour, the reaction solution was washed with diluted hydrochloric acid and then with water and evaporated. The residual crystalline substance was used in the succeeding steps without further purification.

Nicotinamide (2.5 grams) was added to 30 milliliters of tetrahydrofuran (anhydrous), 2.0 grams of sodium hydride (50 percent) was added thereto, the mixture was stirred with refluxing for thirty minutes, cooled, the reaction product as obtained hereinabove was added to this tetrahydrofuran solution, and the mixture was further heated to reflux for three hours. The reaction solution was evaporated to dryness in vacuo, the residue was treated with chloroform to remove insoluble matters, the chloroform-soluble matters were treated with ether, and the crystalline substance obtained therefrom was recrystallized from isopropyl alcohol to give 0.87 grams of the substance (8). Melting point 162° to 164° C.

When the same reaction was conducted by the use of morpholine instead of piperidine, the compound (9) melting at 184° to 187° C. was obtained.

EXAMPLE 5

Synthesis of the compounds (8) and (9)

2-Amino-4-chloro-6-(2,5-dichlorophenyl)-s-triazine (1.3 grams) and 2.0 grams of piperazine were stirred with refluxing for two hours in 20 milliliters of dioxane. The reaction solution was evaporated to dryness in vacuo, water was added to the residue, crystals thereby separated out were collected by filtration, and washed with methanol to give 1.47 grams of 2-amino-4-piperazino-6-(2,5-dichlorophenyl)-s-triazine, melting at 194° to 195° C.

The product obtained hereinabove (1.70 grams) and 3.00 grams of nicotinic acid anhydride were heated to reflux for 3.5 hours in 20 milliliters of dioxane. The reaction solution was cooled, crystals separated out therefrom were discarded by filtration, the mother liquor was evaporated to dryness in vacuo, 50 percent aqueous methanol was added to the residue, crystals separated out therefrom were collected by filtration, and recrystallized from isopropyl alcohol to give 1.04 grams of the substance (8), melting point 162° to 164° C.

When the same reaction was carried out by the use of morpholine instead of piperidine, the substance (9) was obtained. Melting point 184° to 187° C.

EXAMPLE 6

In a manner analogous to the preceding Examples, the following compounds are prepared:

2-(3,4-dichlorophenyl)-4-nicotinoyl-6-pyrrolidino-s-triazine
2-(3,4-dichlorophenyl)-4-morpholino-6-nicotinoyl-s-triazine
2-(2-chlorophenyl)-4-nicotinoyl-6-piperazino-s-triazine
2-(2-chlorophenyl)-4-morpholino-6-nicotinoyl-s-triazine
2-(2-chlorophenyl)-4-nicotinoyl-6-pyrrolidino-s-triazine
2-butylamino-4-(3,4-dichlorophenyl)-6-nicotinoyl-s-triazine
2-(3,4-dichlorophenyl)-4-diethylamino-6-nicotinoyl-s-triazine
2-(2,5-dichlorophenyl)-4-nicotinoyl-6-piperazino-s-triazine
2-(2,5-dichlorophenyl)-4-morpholino-6-nicotinoyl-s-triazine
2-(4-fluorophenyl)-4-dimethylamino-6-nicotinoyl-s-triazine
2-(4-hydroxyphenyl)-4-morpholino-6-nicotinoyl-s-triazine
2-(4-aminophenyl)-4-nicotinoyl-6-pyrrolidino-s-triazine
2-(2-methylphenyl)-4-nicotinoyl-6-pyrrolidino-s-triazine
2-(4-methoxyphenyl)-4-nicotinoyl-6-piperazino-s-triazine
2-(2-methoxyphenyl)-4-morpholino-6-nicotinoyl-s-triazine
2-butylamino-4-(2,6-dimethylphenyl)-6-nicotinoyl-s-triazine
2-(3-ethylphenyl)-4-dimethylamino-6-nicotinoyl-s-triazine
2-diethylamino-4-nicotinoyl-6-nitrophenyl-s-triazine
2-(2-allylphenyl)-4-diethylamino-6-nicotinoyl-s-triazine
2-(4-allylphenyl)-4-butylamino-6-nicotinoyl-s-triazine
2-(2-methoxyphenyl)-4-nicotinoyl-6-piperazino-s-triazine
2-(4-methoxyphenyl)-4-nicotinoyl-6-pyrrolidino-s-triazine
2-(4-hydroxyphenyl)-4-nicotinoyl-6-morpholino-s-triazine
2-nicotinoyl-4-(3-nitrophenyl)-6-piperazino-s-triazine
2-(3-allylphenyl)-4-morpholino-6-nicotinoyl-s-triazine
2-(3-ethylphenyl)-4-dimethylamino-6-nicotinoyl-s-triazine
2-(2-methylphenyl)-4-dimethylamino-6-nicotinoyl-s-triazine
2-(4-methoxyphenyl)-4-diethylamino-6-nicotinoyl-s-triazine
2-(4-aminophenyl)-4-dimethylamino-6-nicotinoyl-s-triazine
2-(4-hydroxyphenyl)-4-diethylamino-6-nicotinoyl-s-triazine

What is claimed:

1. A compound of the formula

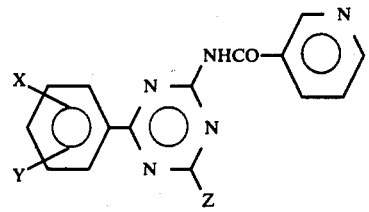

wherein
X is halogen, hydroxy, lower alkyl, lower alkenyl, lower alkoxy, nitro or amino;
Y is hydrogen, halogen, hydroxy, lower alkyl, lower alkenyl, lower alkoxy, nitro or amino; and
Z is mono-(lower alkyl)amino, di-(lower alkyl)amino, piperidino, piperazino, pyrrolidino, or morpholino.

2. The compound according to claim 1, wherein X is halogen and Y is hydrogen or halogen.

3. The compound according to claim 1, wherein X is chlorine and Y is hydrogen or chlorine.

4. The compound according to claim 1, wherein Y is hydrogen and X is fluorine.

5. The compound according to claim 1, 2, 3 or 4 wherein Z is dimethylamino, diethylamino or butylamino.

6. A pharmaceutical composition for the treatment of rheumatism or allergic nephritis, which comprises an effective amount of a compound or pharmaceutically acceptable salt thereof according to claim 1 in combination with a pharmaceutically acceptable inert diluent or carrier therefor.

7. A method of treating a human or animal suffering from rheumatism or allergic nephritis, which comprises administering to the sufferer an effective amount of a compound or pharmaceutically acceptable salt thereof according to claim 1.